US010898125B2

(12) United States Patent
Givon et al.

(10) Patent No.: US 10,898,125 B2
(45) Date of Patent: Jan. 26, 2021

(54) DEEP LEARNING ARCHITECTURE FOR COGNITIVE EXAMINATION SUBSCORE TRAJECTORY PREDICTION IN ALZHEIMER'S DISEASE

(71) Applicant: THE CHARLES STARK DRAPER LABORATORY, INC., Cambridge, MA (US)

(72) Inventors: Lev E. Givon, Cambridge, MA (US); Laura Jane Mariano, Somerville, MA (US); Abraham Schneider, Andover, MA (US); John Irvine, Somerville, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 0 days.

(21) Appl. No.: 16/748,717

(22) Filed: Jan. 21, 2020

(65) Prior Publication Data
US 2020/0229753 A1    Jul. 23, 2020

Related U.S. Application Data

(63) Continuation of application No. 15/967,673, filed on May 1, 2018, now abandoned.
(Continued)

(51) Int. Cl.
*G06K 9/00* (2006.01)
*A61B 5/00* (2006.01)
(Continued)

(52) U.S. Cl.
CPC .......... *A61B 5/4088* (2013.01); *A61B 5/4842* (2013.01); *A61B 5/7267* (2013.01);
(Continued)

(58) Field of Classification Search
CPC ... A61B 5/4088; A61B 5/4842; A61B 5/7267; A61B 5/7275; A61B 5/743; G06N 3/04;
(Continued)

(56) References Cited

U.S. PATENT DOCUMENTS

| | | | |
|---|---|---|---|
| 6,063,028 A | | 5/2000 | Luciano |
| 9,687,199 B2 * | | 6/2017 | Ithapu ............... A61B 5/055 |

(Continued)

FOREIGN PATENT DOCUMENTS

| | | |
|---|---|---|
| CA | 2565646 A1 | 4/2008 |
| WO | 2011051955 A2 | 5/2011 |
| WO | 2016110804 A1 | 7/2016 |

OTHER PUBLICATIONS

International Search Report and Written Opinion in application No. PCT/US2018/030369 dated Jul. 30, 2018.
(Continued)

*Primary Examiner* — Xin Jia
(74) *Attorney, Agent, or Firm* — Lando & Anastasi, LLP

(57) ABSTRACT

A method of predicting progression of a cognitive state in a subject is disclosed including obtaining a neuroimage of the subject, acquiring a data sample from the neuroimage, selecting a time at which to predict progression of the cognitive state, and performing a calculation on the data sample by a transformation function to determine data associated with multiple cognitive metrics. A method of evaluating a cognitive state of a subject is also disclosed including providing a convolutional neural network, training the convolutional neural network with reference data to construct a transformation function, using the transformation function to predict multiple cognitive metrics from a subject data sample and a selected time, and determining the cognitive state of the subject from the predicted cognitive metrics. A cognitive evaluation system is also disclosed including a memory, a processor, and a cognitive state
(Continued)

prediction component configured to program the processor with a transformation function.

23 Claims, 6 Drawing Sheets

Related U.S. Application Data

(60) Provisional application No. 62/492,785, filed on May 1, 2017.

(51) Int. Cl.
    *G16H 30/20*     (2018.01)
    *G16H 50/20*     (2018.01)
    *G06N 3/08*     (2006.01)
    *G06N 3/04*     (2006.01)
    *G06T 7/00*     (2017.01)

(52) U.S. Cl.
    CPC ............ *A61B 5/7275* (2013.01); *A61B 5/743* (2013.01); *G06N 3/04* (2013.01); *G06N 3/08* (2013.01); *G06T 7/0014* (2013.01); *G16H 30/20* (2018.01); *G16H 50/20* (2018.01); *G06T 2207/20076* (2013.01); *G06T 2207/20081* (2013.01); *G06T 2207/20084* (2013.01); *G06T 2207/30016* (2013.01)

(58) Field of Classification Search
    CPC ............ G06N 3/08; G06T 2207/20076; G06T 2207/20081; G06T 2207/20084; G06T 2207/30016; G06T 7/0014; G16H 30/20; G16H 50/20
    See application file for complete search history.

(56) References Cited

U.S. PATENT DOCUMENTS

| | | | |
|---|---|---|---|
| 2011/0119212 A1* | 5/2011 | De Bruin | A61B 5/00 706/12 |
| 2012/0053447 A1* | 3/2012 | Duchesne | A61B 5/055 600/410 |
| 2016/0262680 A1* | 9/2016 | Martucci | A61B 5/4833 |
| 2019/0272922 A1* | 9/2019 | Albright | G06K 9/00536 |

OTHER PUBLICATIONS

Payan et al. "Predicting Alzheimer's disease: a neuroimaging study with 3D convolutional neural networks", Cornell University Library (2015), pp. 1-9.
Zhou et al. "Modeling disease progression via multi-task learning", NeuroImage (2013) vol. 78, pp. 233-248.
Stonnington et al. "Predicting Clinical Scores from Magnetic Resonance Scans in Alzheimer's Disease", Neuroimage (2010), vol. 51 No. 4, pp. 1405-1413.
Walhovd et al. "Multi-modal imaging predicts memory performance in normal aging and cognitive decline", Neurobiology of Aging (2010), vol. 31 No. 7, pp. 1107-1121.
Wang et al. "Sparse Multi-Task Regression and Feature Selection to Identify Brain Imaging Predictors for Memory Performance", IEEE International Conference on Computer Vision (2011), pp. 557-562.
Zhang et al. "Multi-Modal Multi-Task Learning for Joint Prediction of Clinical Scores in Alzheimer's Disease", Multimodal Brain Image Analysis, Springer-Verlag Berlin Heidelberg (2011), pp. 60-67.
Wan et al. "Sparse Bayesian Multi-Task Learning for Predicting Cognitive Outcomes from Neuroimaging Measures in Alzheimer's Disease", IEEE Computer Society Conference on Computer Vision and Pattern Recognition (2012), pp. 1-8.

* cited by examiner

DEEP LEARNING ARCHITECTURE FOR COGNITIVE EXAMINATION SUBSCORE TRAJECTORY PREDICTION IN ALZHEIMER'S DISEASE

CROSS-REFERENCE TO RELATED APPLICATIONS

This application claims priority under 35 U.S.C. § 120 as a continuation of U.S. patent application Ser. No. 15/967,673, titled "DEEP LEARNING ARCHITECTURE FOR COGNITIVE EXAMINATION SUBSCORE TRAJECTORY PREDICTION IN ALZHEIMER'S DISEASE," filed May 1, 2018, which claims priority under 35 U.S.C. § 119 to U.S. Provisional Patent Application No. 62/492,785 titled "DEEP LEARNING ARCHITECTURE FOR COGNITIVE EXAMINATION SUBSCORE TRAJECTORY PREDICTION IN ALZHEIMER'S DISEASE" filed on May 1, 2017. Each of these applications is herein incorporated by reference in its entirety for all purposes.

FIELD OF TECHNOLOGY

Aspects and embodiments disclosed herein relate to systems and methods for cognitive examination. In particular, the systems and methods disclosed herein relate to cognitive examination subscore trajectory prediction in Alzheimer's disease.

SUMMARY

In one aspect, there is provided a method of predicting progression of a cognitive state in a subject. The method may comprise obtaining a neuroimage of the subject, acquiring a data sample from the neuroimage of the subject including a first set of values associated with a plurality of physiological features, selecting a predetermined time at which to predict progression of the cognitive state of the subject, and performing at least one calculation on the first set of values using a transformation function. The calculation may be performed to produce a second set of values including a discrete value associated with each cognitive metric of a plurality of cognitive metrics at the predetermined time. The method may further include presenting the discrete value for each cognitive metric at the predetermined time on a display, thereby predicting progression of the cognitive state of the subject.

In accordance with certain embodiments, the transformation function can be constructed by receiving a data set from a reference population and training a convolutional neural network using the data set from the reference population. The data set from the reference population may include a first data set associated with a respective plurality of physiological features of the reference population and a second data set associated with a respective plurality of cognitive metrics of the reference population. The first data set and the second data set may be correlated by a respective time value. The method may comprise training the convolutional neural network using the data set from the reference population such that the convolutional neural network is adjusted in response to input from the first data set, the second data set, and the respective time values to construct the transformation function.

In some embodiments, obtaining the neuroimage of the subject comprises exposing the subject to a neuroimaging platform to generate the neuroimage.

The method may comprise determining whether the subject is at risk for a mild cognitive impairment or Alzheimer's disease at the predetermined time based on the presentation of the discrete value for each cognitive metric. In certain embodiments, the method may further comprise determining a course of treatment for the subject based on a prognosis of risk of mild cognitive impairment or Alzheimer's disease.

The method may further comprise selecting a discrete value of a cognitive metric on the display to determine a respective value of the first set of values and a respective physiological feature.

In accordance with certain embodiments, the method may comprise selecting the predetermined time to be up to ±36 months. The method may comprise selecting the predetermined time to be up to 36 months.

In some embodiments, the plurality of cognitive metrics include at least one of memory, practice, orientation, and language metrics. For instance, plurality of cognitive metrics may be selected from word recall, verbal commands, constructional praxis, delayed word recall, naming objects, ideation praxis, orientation, word recognition, test instructions recall, comprehension, word finding in speech, spoken language ability, number cancelation, and combinations thereof.

In accordance with another aspect, there is provided a method of evaluating a cognitive state of a subject. The method may comprise providing a network of layers interconnected to form a convolutional neural network, receiving reference data, training the convolutional neural network using the reference data, receiving a data sample from the subject including an input set of values associated with a plurality of physiological features, selecting a predetermined time at which to evaluate the cognitive state of the subject and determining a value for the selected predetermined time, and providing the input set of values and the value for the selected predetermined time to a transformation function. The interconnected layers may comprise a plurality of successive convolution layers and a plurality of fully connected layers. In some embodiments, the reference data may include a first data set associated with a plurality of physiological features and a second data set associated with a plurality of cognitive metrics, the first data set and the second data set being correlated by a respective time value. The method may comprise training the convolutional neural network using the reference data such that the plurality of successive convolution layers and the plurality of fully connected layers are adjusted in response to input from the first data set, the second data set, and the respective time values to construct a transformation function. The method may comprise providing the input set of values and the value for the selected predetermined time to the transformation function, such that the transformation function is trained to predict a respective discrete value for each cognitive metric of the plurality of cognitive metrics from the input set of values and the value for the selected predetermined time. The method may further comprise determining the cognitive state of the subject at the selected predetermined time based on the predicted discrete values of the plurality of cognitive metrics.

In accordance with certain embodiments, training the convolutional neural network may comprise processing the first data set, the second data set, and the respective time values through a training mode configured to train a computer and construct the transformation function.

The method may further comprise presenting the predicted discrete value for each of the cognitive metrics on a display.

In accordance with some embodiments, the method may further comprise predicting the respective discrete value for each of the cognitive metrics by performing at least one calculation. The calculation may include adjusting the plurality of successive convolution layers in response to input from the input set of values to produce a plurality of convolution layer outputs and adjusting the plurality of fully connected layers in response to the value for the selected predetermined time and the plurality of convolution layer outputs to produce the respective discrete value for each of the cognitive metrics.

The method may further comprise receiving a second data sample from the subject at a later time and performing the at least one calculation to produce a second respective discrete value for each of the cognitive metrics. In some embodiments, the method may comprise training the convolutional neural network using a subject data set including the data sample, the second data sample, the respective discrete value for each of the cognitive metrics, and the second respective discrete value for each of the cognitive metrics to construct a customized transformation function.

In accordance with certain embodiments, the method may comprise selecting the predetermined time to be up to ±36 months. The method may comprise selecting the predetermined time to be up to 36 months.

In some embodiments, the plurality of cognitive metrics include at least one of memory, practice, orientation, and language metrics. For instance, plurality of cognitive metrics may be selected from word recall, verbal commands, constructional praxis, delayed word recall, naming objects, ideation praxis, orientation, word recognition, test instructions recall, comprehension, word finding in speech, spoken language ability, number cancelation, and combinations thereof.

In accordance with another aspect, there is provided a cognitive evaluation system for predicting progression of a cognitive state of a subject. The system may comprise a memory and one or more processors coupled to the memory. The memory may store a reference data set including a first data set associated with a plurality of physiological features and a second data set associated with a plurality of cognitive metrics, the first data set and the second data set being correlated by a respective time value. The one or more processors may be configured to execute a cognitive state prediction component. The cognitive state prediction component may be configured to program the processor to receive a data sample from the subject, the data sample including a first set of values associated with a respective plurality of physiological features of the subject, receive a time value corresponding to a selected predetermined time at which to evaluate the cognitive state of the subject, provide the first set of values and the time value to a transformation function, and perform at least one calculation using the transformation function to predict a second set of values including a discrete value for each cognitive metric of a plurality of cognitive metrics from the first set of values and the time value. In some embodiments, the cognitive state prediction component may further be configured to display the discrete value for each cognitive metric on a display.

The cognitive state prediction component may be configured to construct the transformation function by receiving the reference data set and training the cognitive state prediction component using the reference data set such that a convolutional neural network is adjusted in response to input from the reference data set to construct the transformation function.

In accordance with certain embodiments, the cognitive state prediction component may further be configured to program the processor to determine a probability of whether the subject is at risk for a mild cognitive impairment or Alzheimer's disease at the predetermined time based on the discrete value for each cognitive metric. The cognitive state prediction component may further be configured to program the processor to display the probability on the display.

Still other aspects, embodiments, and advantages of these example aspects and embodiments are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Examples and embodiments disclosed herein may be combined with other embodiments and are not necessarily mutually exclusive. Such disclosure is intended to indicate that a particular feature, structure, or characteristic described may be included in at least one embodiment.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
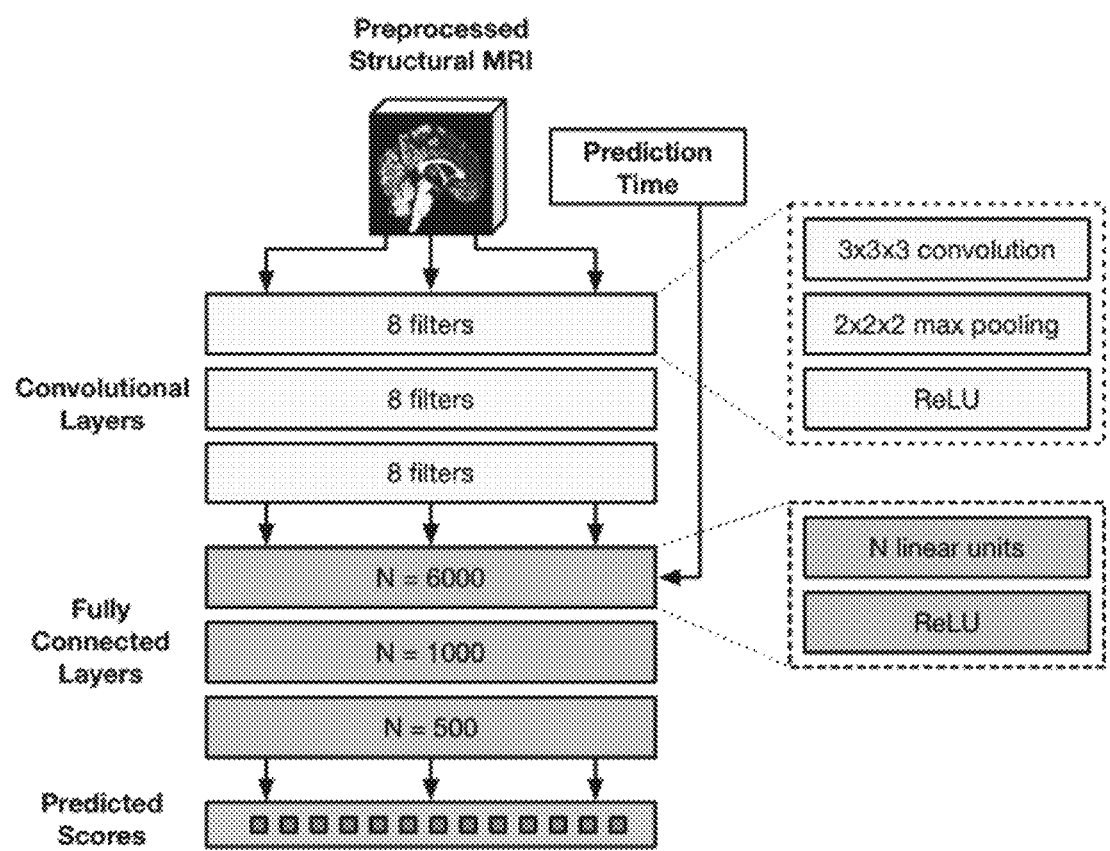
FIG. 1 is a schematic diagram of a convolutional neural network architecture for cognitive subscore prediction, according to one embodiment.

Early phase and differential diagnoses of neurological and neurodegenerative disorders can be challenging. An accurate diagnosis is particularly important in early phases of the disorder, when it is still appropriate to prescribe certain treatment. Current clinical methods for diagnosing these disorders include evaluating neuroimages, biomarkers, and cognitive exam results of the patient. However, due to the similarities between disorders at early phases it is desirable to predict the patient's future trajectory based on current results. Different prediction methods have been developed and implemented in clinical practice, but they are generally directed at predicting a specific cognitive metric from one biological feature or predicting a cumulative result without providing discrete element predictions.

For example, certain techniques for prediction of cognitive scores for Alzheimer's patients from neuroimaging and other biomedical data may utilize stepwise regression, relevance vector regression, multi-task learning, or support vector machines. These approaches, however, are equipped to either only predict the aggregate score of a cognitive exam (the sum of the subscores of the examination's individual questions) rather than the individual subscores, or predict only a single metric such as memory performance. Moreover, these techniques typically rely upon additional preprocessing of input neuroimaging data to reduce its dimensionality by explicitly selecting specific features to relate to cognitive subscores.

Methods disclosed herein of predicting future cognitive states may be implemented for diagnosis of a disease or disorder and/or design of a targeted treatment. In some embodiments, methods disclosed herein may be used to identify progressions of different disease or disorder subtypes, for example, distinguishing between Alzheimer's and non-Alzheimer's dementias. The methods may be implemented for better screening of patients, to assess selectively effective drugs or therapies, to quantify impact of new drugs or therapies on different disease subtypes, or to develop optimally targeted therapies.

Prediction of multiple cognitive exam metrics from a neuroimage with minimal or no preprocessing can yield better results than aggregate score predictions. Conventional methods do not predict individual cognitive subscore trajectories rather than aggregate exam scores. By predicting individual cognitive metrics, for example, question subscores, the methods disclosed herein can provide a significantly more informative assessment of the progression of the patient's neurological state. In certain instances, the methods can predict how the different aspects of a patient's cognitive profile measured by each question in a set of questions will evolve. An aggregate score prediction cannot provide such information. Additionally, a prediction based on an isolated biological feature cannot provide results for the multiple cognitive metrics.

Thus, in one aspect, there is provided a method of evaluating a cognitive state or predicting progression of a cognitive state in a subject capable of predicting a discrete value for multiple cognitive metrics. Such a method could be used to determine whether a patient is at risk for developing a disease and predict patient responses to new therapies for the purposes of trial screening and personalized therapy planning. The method may include obtaining a neuroimage of the subject, acquiring a data sample from the neuroimage of the subject, selecting a predetermined time at which to predict progression of the cognitive state of the subject, and performing at least one calculation on the neuroimage data sample to predict a plurality of cognitive metrics at the predetermined time.

Several methods may be employed for obtaining a neuroimage of the subject. Generally, the neuroimage may be obtained by exposing the subject to a neuroimaging platform. Suitable neuroimaging platforms include magnetic resonance imaging (MRI), for example structural MRI (sMRI) or functional MRI (fMRI), positron emission tomography (PET) scanning, computerized tomography (CT) scanning, Diffusion Tensor Imaging (DTI), in vivo Magnetic Resonance Spectroscopy (MRS), and combinations thereof. In certain instances, the subject data can be obtained from genetic data. The selected data may be dependent on the reference data used for creation of the transformation function.

Methods disclosed herein may comprise constructing a transformation function to process sample data. The transformation function may be constructed by a machine learning architecture. Existing architectures may not have been applied to concurrent prediction of multiple cognitive metrics. Some existing methods for predicting aggregate cognitive exam scores utilize explicitly selected biomarkers such as cortical thickness of different brain regions or volumes of white matter/gray matter/cerebrospinal fluid. By contrast, the systems and methods disclosed herein relate to a deep learning architecture design that may, in certain embodiments, reduce or eliminate the need for explicit feature selection.

Deep learning architectures may be used for diagnosing neurological disorders or cognitive impairment from neuroimaging data. Deep learning is a machine learning method based on feature learning, a technique that uses training functions to define and improve the learning architecture. Feature learning can be tuned to automatically discover the representations needed for feature detection or classification from raw data, replacing manual feature engineering methods. The architecture may learn multiple levels of representations that correspond to different levels of abstraction, forming a hierarchy of concepts. In general, deep learning architectures function by using a cascade of multiple layers of nonlinear processing units for feature extraction and transformation. Each successive layer may use the output from the previous layer as input. Different layers may perform different kinds of transformations on their inputs. The architecture may function in a supervised or unsupervised manner.

In some embodiments, deep learning architecture models may be selected to mimic information processing and communication patterns in a biological nervous system. Such an architecture is termed an artificial neural network. An artificial neural network can be constructed to include a collection of connected kernels, or "neurons" as they are often referred to in neural networks, which transmit the cascading signals. The artificial neural network can be tuned to progressively improve performance on recognition by training with representative data. The tuning can be performed without recognition-specific programming. In some embodiments, the neurons may be associated with a weight that adjusts as learning proceeds.

In general, kernels are functions that provide a mapping between different vector spaces. When chosen correctly, kernels may perform an implicit dot product between two vectors in the higher dimensional space without actually having to go into that space. Datasets with non-linear class boundaries in raw data space may become linearly separable when they have been transformed appropriately. However, given the high (and potentially infinite) dimensionality, explicitly mapping the data to the feature space may be computationally intensive. Instead, a kernel function may be employed to perform an implicit mapping of the data to the feature space.

The kernel function is an operation that can be applied to the data vectors that is equivalent to computing their inner product after they have been embedded in the feature space without actually having to map them first. Kernel evaluations can therefore be used in place of every inner product operation required by optimization algorithms designed to identify class boundaries in feature space. When applied to artificial neural networks, a different kernel may be chosen for each modality of data. Commonly used kernel functions include those represented by linear kernel functions which compute the dot product between two data vectors and Gaussian Radial Basis Functions, which perform a non-linear mapping of the data into a higher dimensional feature space.

Suitable deep learning architecture models include group method data handling (GMDH), convolutional neural networks (CNN), long short-term memory (LSTM), deep reservoir computing and deep echo state networks (deepESNs), deep belief networks (DBN), large memory storage and retrieval neural networks (LAMSTAR), stacked de-noising auto-encoders, deep stacking networks (DSN), for example, tensor DSNs, spike and slap restricted Boltzman machines (ssRBM), compound hierarchical-deep models, deep predictive coding networks (DPCN), multilayer kernel machines (MKM), and networks with other memory structures, for example, neural Turing machines, semantic hashing networks, memory networks, pointer networks, and encoder-decoder networks.

In some embodiments, the deep learning architecture model is selected to operate with minimal or no preprocessing. The method may comprise providing a network of layers, for example, interconnected to form a CNN. CNNs are a class of deep feed-forward artificial neural networks which can operate with minimal or no preprocessing. In general, CNNs are made up of multiple layers, including input, output, and hidden layers. The hidden layers can be classified as convolution layers, pooling layers, fully connected layers, and normalization layers. Convolution layers typically apply a convolution operation to the input, passing the result to the next layer. Weights may be shared in the convolution layers, reducing memory footprint and improving performance of the transformation function. Pooling layers may combine the outputs of previous layers or clusters of neurons into one layer or neuron before passing the result to the next layer. Pooling layers in the operation may be local or global. Fully connected layers can connect a plurality of neurons in one layer to a respective plurality of neurons in another layer. In some embodiments, fully connected layers may operate similar to a multi-layer perception neural network (MLP). In an exemplary embodiment, the CNN may comprise a plurality of successive convolution layers and a plurality of fully connected layers. The transformation function may include pooling of clusters of neurons, for example, in the convolution layers.

In accordance with certain embodiments, the transformation function can be constructed by receiving a data set from a reference population and training a network architecture using the data set from the reference population. For instance, the architecture may be trained such that it is adjusted in response to input from the reference data to construct the transformation function. Training the artificial network may comprise adjusting one or more layers in response to the reference data. For example, in some embodiments, successive convolution layers and fully connected layers may be adjusted in response to the reference data.

Systems and methods described herein may further employ machine learning techniques for multivariate regression, such as support vector regression. Additionally, systems and methods described herein may formulate the prediction task as a multi-task learning problem to enable leveraging regression/optimization strategies, including, but not limited to, Multiple Measurement Vector (MMV) Focal Underdetermined System Solver, Temporal Group Lasso, MMV Basis Pursuit, Simultaneous Orthogonal Matching Pursuit, Multi-Task Compressive Sensing, Temporal MMV Sparse Bayesian Learning, and Ridge Regression. Furthermore, to increase the value of the subscore predictions produced by the methods disclosed herein, the prediction confidence may be quantified using techniques such as those taught by Yarin Gal and Zoubin Ghahramani in "Dropout as a Bayesian Approximation: Representing Model Uncertainty in Deep Learning," which is herein incorporated by reference in its entirety for all purposes.

As with many convolutional neural network architectures, finding appropriate parameters of the optimization algorithm used in training may require significant experimentation. Individual neuroimaging and cognitive score data points may contain potential interrelationships. For example, multiple physiological features and cognitive scores may be associated with the same patient. Certain aspects of cognition measured by individual questions in cognitive examinations may be more related to each other than to those quantified by other questions. Some embodiments may employ a customized loss function (for example, a function that weights discrepancies of different cognitive metrics to reflect their interrelatedness) or incorporation of metric learning that could explore data interrelatedness to obtain more accurate predictions. Loss functions and optimization algorithms other than those described herein may be used.

In accordance with certain embodiments, training the artificial neural network may comprise processing the reference data through a training mode configured to train a computer and construct the transformation function. The training mode can improve function of the computer by improving the artificial neural network performance as previously described. The computer may be comprised in a system for predicting progression of a cognitive state of a subject. The system may comprise a memory storing a reference data set and one or more processors coupled to the memory and configured to execute a cognitive state prediction component.

Figure 2:
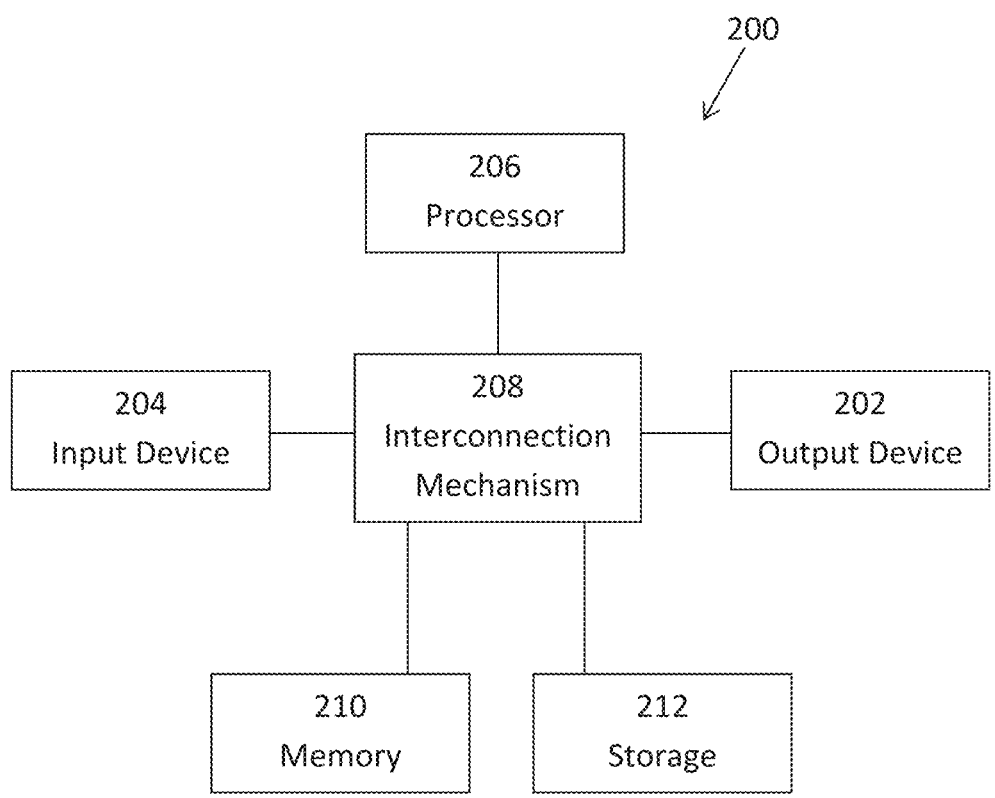
FIG. 2 is a block diagram of an exemplary system upon which various aspects of the disclosed embodiments may be implemented.

Referring to FIG. 2, there is illustrated a block diagram of one example of computing components forming a system 200 which may be configured to implement one or more aspects disclosed herein. For example, the system 200 may be communicatively coupled to a PCU or included within a PCU and configured to perform a function as described herein.

The system 200 may include for example a general-purpose computing platform such as those based on Intel PENTIUM-type processor, Motorola PowerPC, Sun Ultra-SPARC, Texas Instruments-DSP, Hewlett-Packard PA-RISC processors, or any other type of processor. System 200 may include specially-programmed, special-purpose hardware, for example, an application-specific integrated circuit (ASIC). Various aspects of the present disclosure may be implemented as specialized software executing on the system 200 such as that shown in FIG. 2.

The system 200 may include a processor/ASIC 206 connected to one or more memory devices 210, such as a disk drive, memory, flash memory or other device for storing data. Memory 210 may be used for storing programs and data during operation of the system 200. In some embodiments, receiving reference data may be performed once and the received data stored in the memory 210. Alternatively, receiving reference data may be repeated as necessary to adjust the transformation function.

Components of the computer system 200 may be coupled by an interconnection mechanism 208, which may include one or more buses (for example, between components that are integrated within a same machine) and/or a network (for example, between components that reside on separate machines). The interconnection mechanism 208 may enable communications (for example, data, instructions) to be exchanged between components of the system 200. Further, in some embodiments the interconnection mechanism 208 may be disconnected during servicing of a PDU.

The system 200 may also include one or more input devices 204, which may include for example, a keyboard, a mouse, or a touch screen. An input device 204 may be used, for example, to configure the measurement system or to provide input parameters. The system 200 may include one or more output devices 202, which may include for example a display. In addition, the computer system 200 may contain one or more interfaces (not shown) that may connect the computer system 200 to a communication network, in addition or as an alternative to the interconnection mechanism 208.

The system 200 may include a storage system 212, which may include a computer readable and/or writeable nonvolatile medium in which signals may be stored to provide a program to be executed by the processor or to provide information stored on or in the medium to be processed by the program. The medium may, for example, be a disk or flash memory and in some examples may include RAM or other non-volatile memory such as EEPROM. In some embodiments, the processor may cause data to be read from the nonvolatile medium into another memory 210 that allows for faster access to the information by the processor/ASIC than does the medium. This memory 210 may be a volatile, random access memory such as a dynamic random access memory (DRAM) or static memory (SRAM). It may be located in storage system 212 or in memory system 210. The processor 206 may manipulate the data within the integrated circuit memory 210 and then copy the data to the storage 212 after processing is completed. A variety of mechanisms are known for managing data movement between storage 212 and the integrated circuit memory element 210, and the disclosure is not limited thereto. The disclosure is not limited to a particular memory system 210 or a storage system 212.

The system 200 may include a general-purpose computer platform that is programmable using a high-level computer programming language. The system 200 may also be implemented using specially programmed, special purpose hardware, e.g. an ASIC. The system 200 may include a processor 206, which may be a commercially available processor such as the well-known Pentium class processor available from the Intel Corporation. Many other processors are available. The processor 206 may execute an operating system which may be, for example, a Windows operating system available from the Microsoft Corporation, MAC OS System X available from Apple Computer, the Solaris Operating System available from Sun Microsystems, or UNIX and/or LINUX available from various sources. Many other operating systems may be used.

The processor and operating system together may form a computer platform for which application programs in high-level programming languages may be written. It should be understood that the disclosure is not limited to a particular computer system platform, processor, operating system, or network. Also, it should be apparent to those skilled in the art that the present disclosure is not limited to a specific programming language or computer system. Further, it should be appreciated that other appropriate programming languages and other appropriate computer systems could also be used.

Various aspects and functions described herein in accordance with the disclosure may be implemented as hardware, software, firmware, or any combination thereof. Aspects in accordance with the disclosure may be implemented within methods, acts, systems, system elements, and components using a variety of hardware, software, or firmware configurations. Aspects in accordance with the disclosure may be implemented as specially-programmed hardware and/or software.

In accordance with certain embodiments, the transformation function may be constructed by receiving a reference data set and training a network accordingly. The cognitive state prediction component may be configured to construct the transformation function by receiving the reference data set and training the cognitive state prediction component using the reference data set, such that the artificial neural network is adjusted in response to input from the reference data set. The processor may be programed to perform in response to the transformation function adjustment.

The data set from the reference population may include a first data set associated with a plurality of physiological features of the reference population and a second data set associated with a respective plurality of cognitive metrics of the reference population. The first data set and the second data set may be correlated by a respective time value. The first data set may comprise information from a plurality of features, such that no preselection for a feature was performed. As previously described, preselection of a single feature may be used to predict a cognitive metric, but may not in all cases be used to predict two or more cognitive metrics. The systems and methods disclosed herein may be used to predict a plurality of cognitive metrics from data sample. Additionally, because the reference data includes a time value component, the systems and methods disclosed herein may be used to predict the cognitive metric from a current sample at a future time.

The data set from the reference population may be obtained from research databases, such as the Alzheimer's Disease Neuroimaging Initiative (ADNI). The ADNI database stores validated data including MRI and PET images, genetic information, cognitive test results, metabolites, and cerebrospinal fluid and blood biomarkers. These data may be correlated for each subject by a respective time value indicating the amount of elapsed time between tests. The data from the reference population may include one or more of neuroimages, genetic information, cognitive test results, metabolite concentrations, biomarker concentrations, demographic information (for example, race, ethnicity, gender, age, education, etc.), medical history, or family history. In some embodiments, the physiological features may include physical attributes of the brain, functional attributes of the brain, genetic information, metabolite concentrations, biomarker concentrations, or demographic information.

While the disclosure describes various embodiments specific to Alzheimer's disease, it should be understood that the embodiments described herein are not limited to Alzheimer's disease, but are applicable to other neurodegenerative, neurological, and neurocognitive diseases and disorders. Other diseases and disorders include, for example, Parkinson's Disease, Prion Disease, Motor Neuron Disease, Amyotrophic lateral sclerosis, Multiple sclerosis, Huntington's Disease, Spinocerebellar Ataxia, Spinal Muscular Atrophy, Chronic Traumatic Encephalopathy (CTE), Post-Traumatic Stress Disorder (PTSD), Traumatic Brain Injury (TBI), and Mild Traumatic Brain Injury (MTBI). For instance, a subject returning from war or combat conditions may be monitored for PTSD with a PTSD representative group function, while a subject with a history of multiple concussions and other forms of head injury may be monitored for CTE with a CTE representative group function. Furthermore, the embodiments described herein may be employed for healthy control groups, groups exhibiting a Mild Cognitive Impairment (MCI), or groups that are otherwise not diagnosed as suffering from a neurodegenerative, neurological, or neurocognitive disease.

In accordance with certain embodiments, methods disclosed herein may comprise acquiring or receiving a data sample from the subject. The data sample may be acquired from a neuroimage of the subject or from another origin, for example, genetic information, metabolite concentrations, or biomarker concentrations. In general, the data sample acquired from the subject will match a type used from the reference data to train the transformation function. Accordingly, the data sample may include a set of values associated with a plurality of physiological features. In some embodiments, the data sample is not selective of a single feature.

Systems and methods disclosed herein may accept both current subject data and desired future time of cognitive metric prediction as inputs. The trained network, therefore, may comprise a regression of predicted cognitive metric trajectory onto available subject data and desired prediction times. This may enable the trained network to compute predictions for times in between (or beyond) the cognitive examination times used for training. Thus, methods disclosed herein may comprise selecting a predetermined time at which to predict progression of the cognitive state of the subject. The predetermined time may be selected for diagnosis and/or design of a targeted treatment. In some embodiments, the predetermined time may be up to ±48 months, for example, ±36 months. The method may comprise selecting the predetermined time to be −48 months, −36 months, −30 months, −24 months, −18 months, −12 months, −6 months, −3 months, or −1 month for diagnosis or for design of future treatment. The method may comprise selecting the predetermined time to be 1 month, 3 months, 6 months, 12 months, 18 months, 24 months, 30 months, 36 months, or up to 48 months for prognosis or design of future treatment. A value for the predetermined time may be determined for calculation purposes.

The subject may be suspected of having or developing a neurodegenerative, neurological, and neurocognitive disease or disorder as disclosed herein. The subject may be selected based on, for example, age, medical history, family history, genetic information, or recent psychological performance. In an exemplary embodiment, the subject may be suspected of having or developing Alzheimer's disease. The causes of Alzheimer's disease are believed to come from many sources, including: the accumulation of the protein beta-amyloid outside the nerve cells, the accumulation of the protein tau inside neurons, family history, and within the nervous system, the inability or failure of information to transfer at the synapse. One or more risk factors may be associated with Alzheimer's disease. These may include family history, which may be the result of genetic and/or environmental factors, the presence or level of Apolipoprotein E-ε4, which is one of three forms of the APOE gene and provides the blueprint for a protein that carries cholesterol in the bloodstream, MCI, cardiovascular disease, physical/mental inactivity, high fat diets, and head trauma and/or TBI.

The subject may be an animal, a mammal, a human, or a non-human. The term "subject" is intended to include human and non-human animals, for example, vertebrates, large animals, primates, and research animals (for example, mice, rats, pigs, cats, and dogs). In certain embodiments, the subject is a mammalian subject. In certain embodiments, the subject is a human subject. Although applications with humans are clearly foreseen, veterinary applications, for example, with non-human animals, are also envisaged herein. The subject may generally be selected to match the representative data. In other embodiments, the representative data and/or the transformation function may be selected to match the target subject. The test parameters, for example, neuroimages and cognitive metrics, may correspond to the target subject.

In accordance with certain embodiments, the method may further comprise performing at least one calculation on the set of values associated with the physiological features of the subject using the transformation function constructed from the reference data. This may be achieved by providing the sample data and the predetermined time at which to evaluate the cognitive state of the subject as input values to the transformation function. The transformation function can be trained to predict a respective discrete value for each cognitive metric of a plurality of cognitive metrics from the input data. In an exemplary convolutional neural network, the method may include adjusting a plurality of successive convolution layers in response to input from the subject data to produce a plurality of convolution layer outputs. The plurality of convolution layer outputs, in turn, can be provided to adjust a plurality of fully connected layers together with the predetermined time value. Layers may be adjusted by providing input reference values (for example, as an array of voxels) to kernel or neuron functions and calculating at least one weighting factor for each data sample. The method may thus produce a respective discrete value for each of the cognitive metrics.

In some embodiments, methods disclosed herein may comprise receiving or acquiring an additional data sample from the subject. The additional data sample may be acquired at a later time. The additional data sample may be of the same type, for example, a second or subsequent neuroimage, or of a different type, for example, genetic information. The additional data sample can be used, together with the respective cognitive metric values, to further train the transformation function to produce a customized transformation function. The customized transformation function can be specific to the subject or to a demographic group of the subject.

The cognitive state prediction component may program the processor to receive the data sample from the subject, receive a time value for the selected predetermined time at which to evaluate the cognitive state of the subject, and provide this information to the transformation function as described herein. The cognitive state prediction component may further program the processor to perform at least one calculation using the transformation function to predict cognitive metrics of the subject at the predetermined time, as described herein. In some embodiments, the cognitive state prediction component may program the processor to display the discrete value for each cognitive metric on a display.

Thus, in accordance with certain embodiments, methods disclosed herein may further include presenting the discrete value for each cognitive metric at the predetermined time on a display, thereby predicting progression of the cognitive state of the subject. The cognitive metrics may include at least one metric in the fields of memory, practice, orientation, and language. The cognitive state of the subject may be presented as a point on a 2D or 3D array of two or more cognitive metrics. In an exemplary embodiment, the cognitive metrics may be selected from the Alzheimer's Disease Assessment Scale-cognitive subscale (ADAS-Cog). For example, the cognitive metrics may include word recall, verbal commands, constructional praxis, delayed word recall, naming objects, ideation praxis, orientation, word recognition, test instructions recall, comprehension, word finding in speech, spoken language ability, number cancelation, and combinations thereof. Other suitable cognitive metrics include categories from the Mini-Mental State Examination (MMSE), the Addenbrooke's Cognitive Examination (ACE), the Mental Test Score (MTS), and other multi-question cognitive exams. Each cognitive metric may have a different value range, as understood by one of ordinary skill in the art. Furthermore, the subject's educational background, age, and language should be considered in assessing the value ranges.

In certain embodiments, the method may further comprise selecting a discrete value of a cognitive metric on the display to determine a respective value of the physiological feature. This embodiment may allow for correlation of certain cognitive metrics to one or more physiological features of the subject. This embodiment may be employed to identify and potentially quantify biomarker trajectory changes associated with cognitive decline.

The method may comprise determining the cognitive state of the subject at the selected predetermined time based on the predicted discrete values for the cognitive metrics. The cognitive state of the subject, as determined by the systems and methods disclosed herein, may be normal (healthy), indicate the subject has a mild, moderate, or severe cognitive impairment, or indicate the subject is at risk for a cognitive impairment. The method may comprise determining whether the subject is at risk for a neurodegenerative, neurological, or neurocognitive disease or disorder, for example, by analyzing the presented data. In an exemplary embodiment, the method may comprise determining whether the subject is at risk for a mild cognitive impairment or Alzheimer's disease at the selected predetermined time based on the presentation of the data. The determination of whether the subject is at risk for a disease may be presented as a probability.

In some embodiments, a trained professional, for example, a health provider, physician, or researcher may review the presented data and determine the predicted cognitive state of the subject at the predetermined time. The determination may be made based on threshold values for each cognitive metric, for example, by comparing the cognitive metric results calculated by the training function to known threshold values. The method may further comprise determining a course of treatment for the subject based on the prognosis. In other embodiments, the cognitive state prediction component may be configured to program the processor to determine the cognitive state of the subject at the predetermined time. The cognitive state prediction component may be configured to program the processor to determine whether the subject is at risk for a disease or disorder as disclosed herein. In such embodiments, the cognitive state prediction component may be configured to program the processor to display the cognitive state of the subject and/or probability of whether the subject is at risk for a disease or disorder on the display.

The systems and methods disclosed herein may be run with minimal or no preprocessing of the subject data. However, preprocessing of the reference data used to train the architecture can boost its performance and reduce prediction variability. In an exemplary embodiment, a neuro-image preprocessing pipeline may be employed to register all images to a single 3D template, strip non-brain tissue from the images, correct image geometry and intensity distortions, normalize cognitive metrics to the range [0; 1], perform dropout after convolutional layers to prevent overfitting, cross-validate by t months for $t \in [0, 6, 12, 18, 24, 30, 36]$, and/or normalize pixel intensity to the range [0; 1]. Noticeable differences can be observed in the prediction accuracy for the various cognitive metrics. Additionally, since each cognitive metric may have a different value range, metrics can be standardized to have zero mean and unit variance.

In some embodiments, the neural network architecture can be extended to include more than one physiological feature, for example, sMRI, fMRI, PET, DTI, MRS, genetic data, metabolite concentrations, biomarker concentrations, or demographic information. This embodiment can potentially perform more accurate predictions and correlate the different physiological features to each other or simultaneously to the cognitive metrics. Additionally, should new datasets become available, for example, from drug trials, systems and methods disclosed herein may be capable of extending the existing architecture to enable fine-tuning of the trained network with the additional dataset.

Figure 3:
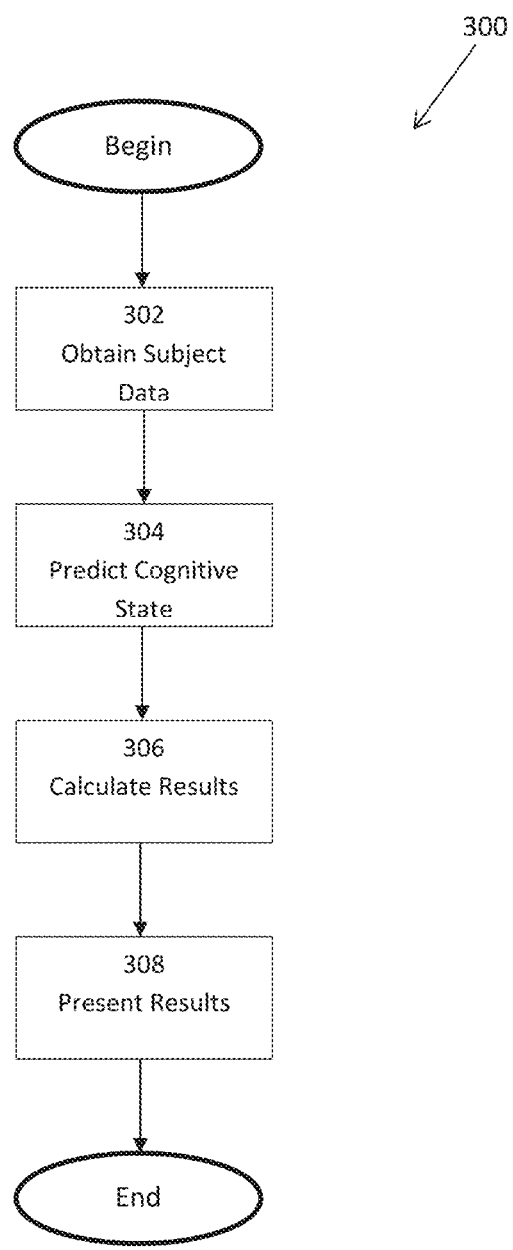
FIG. 3 is a flow diagram of an exemplary cognitive state prediction test process, according to one embodiment.
Figure 4:
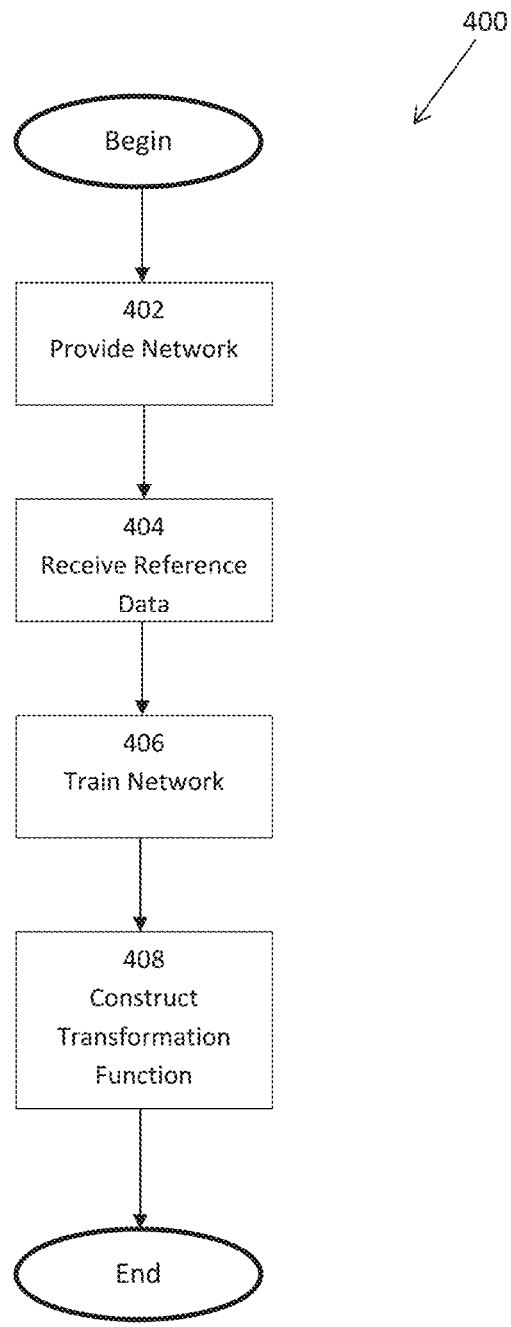
FIG. 4 is a flow diagram of an exemplary transformation function construction process, according to one embodiment.

As described with reference to FIGS. 3 and 4, several embodiments predict a cognitive state of the subject at a selected predetermined time. FIG. 3 illustrates one example cognitive state prediction test process 300 that may be performed by a computer system (for example, executed by processor 206 of computer system 200). The cognitive state prediction process 300 includes the acts of obtaining subject data 302, selecting a time at which to predict the cognitive state of the subject 304, performing at least one calculation on the subject data using a transformation function 306, and presenting the predicted cognitive metrics on a display 308. FIG. 4 illustrates an example transformation function construction process 400 that may also be performed by computer system 200. The transformation function construction process 400 includes providing a neural network 402, receiving reference data 404, training the neural network with the reference data 406, and constructing the transformation function 408. The cognitive state prediction process 300 can be performed after constructing the transformation function 408.

EXAMPLES

Example 1: Prediction of ADAS-Cog Subscores Using Structural MRI Data

An essential part of the current diagnosis process for Alzheimer's disease includes assessment of a patient's cognitive state by measuring responses to several cognitive examinations, for example, using the Alzheimer's Disease Assessment Scale-cognitive subscale (ADAS-Cog). In an exemplary embodiment, systems and methods disclosed herein are employed to accurately predict future trajectories of the cognitive subscores for individual questions comprised by these examinations given a current structural MRI of a patient's brain.

A convolutional neural network (CNN) architecture was designed to accurately predict a subject's 13 subscores for the ADAS-Cog examination up to 4 years into the future given a current structural MRI of the brain. The exemplary architecture is shown in FIG. 1. This architecture includes the following: (a) an input containing a structural MRI (represented as a 3D array of voxels) and a time (represented in number of months after the present time) at which to predict cognitive exam subscores; (b) 3 successive layers, each comprising: (i) convolution with 3×3×3 kernels, a stride of 1, and 0 padding, (ii) maximum pooling with 2×2×2 kernels, a stride of 1, and 0 padding, and (iii) rectified linear activation, where the first convolution layer's input contains the structural MRI; (c) 3 fully connected layers, each comprising: (i) N linear units, and (ii) rectified linear activation, where N=6000, 1000, 500 for the 3 layers, respectively, and the first connected layer's input contains the desired prediction time and the convolution layer outputs; and (d) an output consisting of 13 predicted cognitive subscores.

To prevent overfitting, dropout with a probability of 0.5 was performed after max pooling in every convolutional layer during training. The example method utilized smooth $L_1$ loss to reduce the effects of outliers upon prediction performance. The adaptive learning rate optimization algorithm RMSProp was used for training. The architecture was implemented in PyTorch and trained on Ubuntu Linux 16.04 with NVIDIA Tesla M40 Graphics Processing Units (GPUs).

All sMRI and cognitive data were obtained from the ADNI database. Only 1.5T MRI scans from a quality-controlled subset of the ADNI1 phase of the project were utilized. sMRI scans were minimally preprocessed to remove non-brain tissue, normalize intensities, and register all scans to a single coordinate space. All subscores were normalized to the range [0, 1] prior to training and testing. After training with a representative set of structural MRIs and ADAS-Cog subscores labeled with the interval of time between image acquisition and cognitive examination, the architecture can predict subscores at arbitrary specified future times for a patient given a current structural MRI.

To evaluate the architecture, a 5-fold cross-validation with training and testing data drawn from a set of tuples of sMRI scans, cognitive scores, and time intervals between MRI and cognitive score acquisition was performed. Intervals were multiples of 6 months between 0 and 36. Each fold was stratied to contain equal numbers of subscores for each unique interval. To ensure that each fold contained a sufficient number of tuples for each interval, the folds were drawn from a dataset comprising 1000 entries.

The architecture can successfully predict subscores at arbitrary specified future times for a patient given a current structural MRI. The architecture can be easily adapted for predicting subscores of other cognitive impairments and/or using other examinations to assess cognitive impairment, such as the Mini-Mental State Examination (MMSE).

Example 2: Comparison of Discrete Cognitive Metric Prediction and Aggregate Score Prediction The CNN of Example 1 was used to determine the cognitive subscores in Table 1 (ADAS-Cog subscores) using the patient's current sMRI scan and a future time (in number of months). Intervals were multiples of 6 months between 0 and 36. Each fold was stratied to contain equal numbers of subscores for each unique interval.

TABLE 1

| Cognitive Subscores | | |
| --- | --- | --- |
| Question | Cognitive Subscore | Category |
| Q1 | Word Recall | Learning and Memory |
| Q2 | Verbal Commands | Language Production/Comprehension |
| Q3 | Constructional Praxis | Praxis |
| Q4 | Delayed Word Recall | Learning and Memory |
| Q5 | Naming Objects | Language Production/Comprehension |
| Q6 | Ideation Praxis | Praxis |
| Q7 | Orientation | Orientation |
| Q8 | Word Recognition | Learning and Memory |
| Q9 | Test Instructions Recall | Language Production/Comprehension |
| Q10 | Comprehension | Language Production/Comprehension |
| Q11 | Word Finding in Speech | Language Production/Comprehension |
| Q12 | Spoken Language Ability | Language Production/Comprehension |
| Q13 | Number Cancelation | Learning and Memory |

Figure 5:
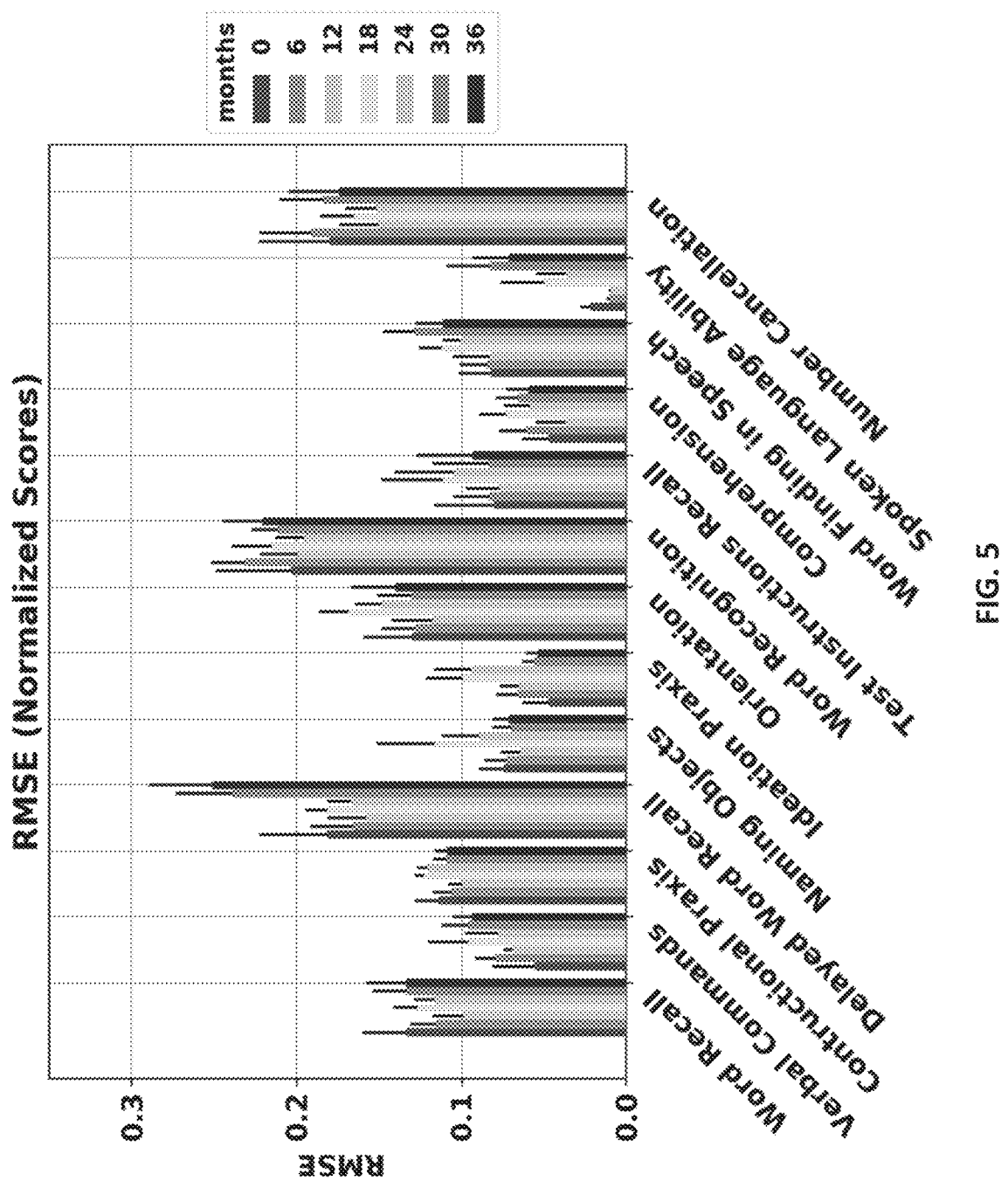
FIG. 5 is a graph of the root mean squared error (RMSE) of the predicted cognitive subscores of Example 2.

The root mean squared error (RMSE) was computed for each of the 13 subscores for each interval. The means and standard errors of the subscore RMSEs computed across all folds are shown in FIG. 5. The means and standard errors across all intervals and subscores varied from 0.009 to 0.251 and from 0.001 to 0.046, respectively, as shown in FIG. 5.

Figure 6:
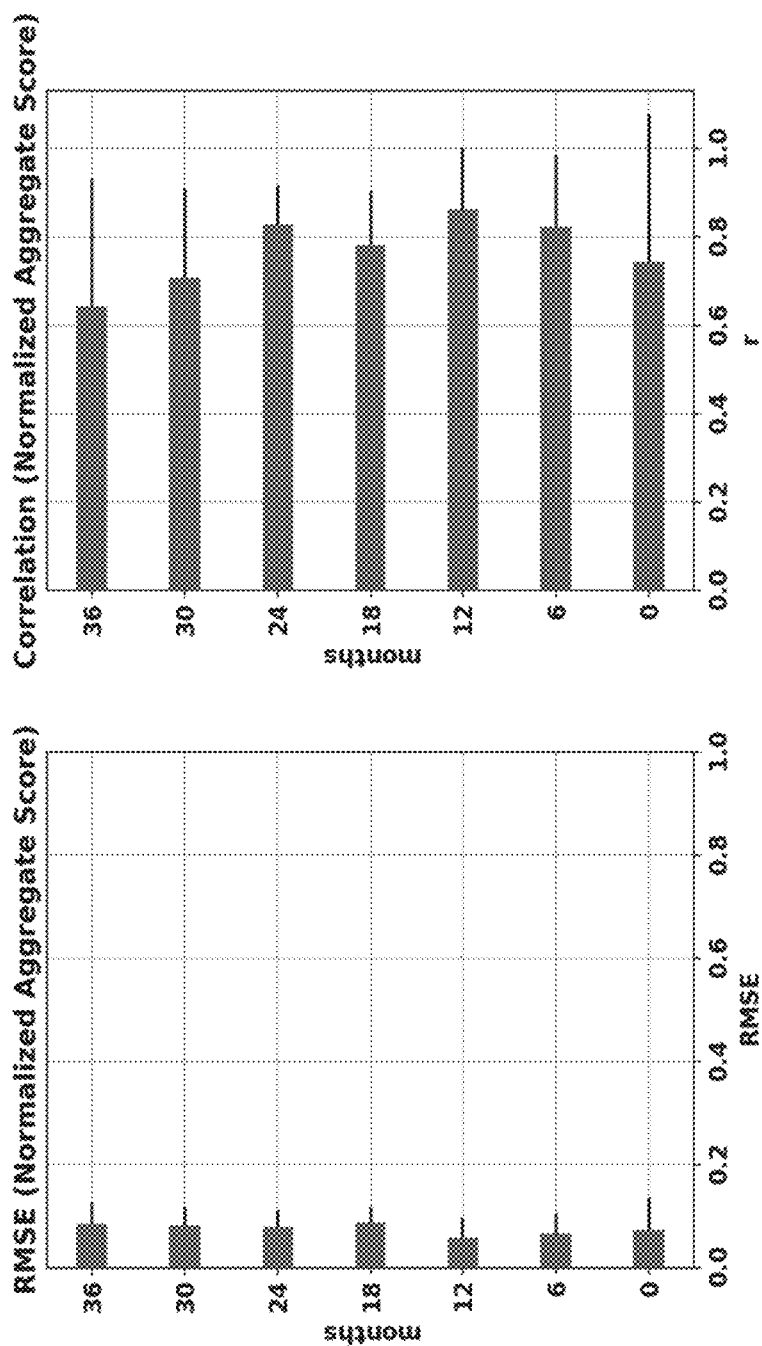
FIG. 6 includes two graphs of the RMSE and Pearson's correlation coefficient of the predicted aggregate scores of Example 2.

To compare the performance of the exemplary network with other approaches that only predict the aggregate score, the RMSE and Pearson's correlation coefficient of the predicted/actual aggregate score normalized to the range [0; 1] were computed (shown in FIG. 6). The latter was obtained by rescaling the normalized subscores to their original respective ranges and normalizing the sum using the highest possible aggregate score. The means and standard errors of the RMSEs of the exemplary method's normalized aggregate score prediction for the intervals considered varied from 0.058 to 0.087 and from 0.014 to 0.028, respectively, as shown in FIG. 6. The means and standard errors of the correlation between predicted and actual aggregate scores across all intervals varied from 0.643 to 0.862 and from 0.040 to 0.149, respectively, as shown in FIG. 6.

The network successfully concurrently predicted multiple cognitive examination subscores from minimally preprocessed structural brain data. Variations in prediction accuracy across the subscores illustrate differences in the relationships between brain structure and specific aspects of cognition that are obscured by prediction of the aggregate score. Thus, the exemplary CNN architecture can predict the trajectories of the 13 subscores comprised by a subject's ADAS-Cog examination results from a current sMRI scan up to 36 months from image acquisition time without resorting to manual feature extraction. Mean performance metrics are within range of those of existing techniques that require manual feature selection and are limited to predicting aggregate scores.

Since the quality of features extracted by CNNs is proportional to the amount of training data and a number of network layers, it is anticipated that deeper variations of the architecture trained on more extensive subsets of the reference population databases will be able to achieve improved performance.

Those skilled in the art should appreciate that the parameters and configurations described herein are exemplary and that actual parameters and/or configurations will depend on the specific application in which the disclosed methods and materials are used. Those skilled in the art should also recognize or be able to ascertain, using no more than routine experimentation, equivalents to the specific embodiments disclosed. For example, those skilled in the art may recognize that the method, and components thereof, according to the present disclosure may further comprise a network or systems or be a component of a system for cognitive examination. It is therefore to be understood that the embodiments described herein are presented by way of example only and that, within the scope of the appended claims and equivalents thereto; the disclosed embodiments may be practiced otherwise than as specifically described. The present systems and methods are directed to each individual feature, system, or method described herein. In addition, any combination of two or more such features, systems, or methods, if such features, systems, or methods are not mutually inconsistent, is included within the scope of the present disclosure. The steps of the methods disclosed herein may be performed in the order illustrated or in alternate orders and the methods may include additional or alternative acts or may be performed with one or more of the illustrated acts omitted.

Further, it is to be appreciated that various alterations, modifications, and improvements will readily occur to those skilled in the art. Such alterations, modifications, and improvements are intended to be part of this disclosure, and are intended to be within the spirit and scope of the disclosure. In other instances, an existing facility may be modified to utilize or incorporate any one or more aspects of the methods and systems described herein. Thus, in some instances, the systems may involve cognitive examination. Accordingly the foregoing description and figures are by way of example only. Further the depictions in the figures do not limit the disclosures to the particularly illustrated representations.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

While exemplary embodiments of the disclosure have been disclosed, many modifications, additions, and deletions may be made therein without departing from the spirit and scope of the disclosure and its equivalents, as set forth in the description.

What is claimed is:

1. A method of predicting progression of a cognitive state in a subject, the method comprising:
   obtaining a neuroimage of the subject;
   acquiring a data sample from the neuroimage of the subject, the data sample including a first set of values associated with a plurality of physiological features;
   selecting a predetermined time at which to predict progression of the cognitive state of the subject;
   performing at least one calculation on the first set of values using a transformation function to produce a second set of values including a discrete value associated with each cognitive metric of a plurality of cognitive metrics at the predetermined time, the transformation function constructed by:
   receiving a data set from a reference population, the data set including a first data set associated with a respective plurality of physiological features of the reference population and a second data set associated with a respective plurality of cognitive metrics of the reference population, the first data set and the second data set being correlated by a respective time value; and
   training a convolutional neural network using the data set from the reference population such that the convolutional neural network is adjusted in response to input from the first data set, the second data set, and the respective time values to construct the transformation function; and
   presenting the discrete value for each cognitive metric at the predetermined time on a display, thereby predicting progression of the cognitive state of the subject.

2. The method of claim 1, wherein obtaining the neuroimage of the subject comprises exposing the subject to a neuroimaging platform to generate the neuroimage.

3. The method of claim 1, further comprising determining whether the subject is at risk for a mild cognitive impairment or Alzheimer's disease at the predetermined time based on the presentation of the discrete value for each cognitive metric.

4. The method of claim 3, further comprising determining a course of treatment for the subject based on a prognosis for risk of mild cognitive impairment or Alzheimer's disease.

5. The method of claim 1, further comprising selecting a discrete value of a cognitive metric on the display to determine a respective value of the first set of values and a respective physiological feature.

6. The method of claim 1, comprising selecting the predetermined time to be up to ±36 months.

7. The method of claim 6, comprising selecting the predetermined time to be up to 36 months.

8. The method of claim 1, wherein the plurality of cognitive metrics include at least one of memory, practice, orientation, and language metrics.

9. The method of claim 8, wherein the plurality of cognitive metrics are selected from word recall, verbal commands, constructional praxis, delayed word recall, naming objects, ideation praxis, orientation, word recognition, test instructions recall, comprehension, word finding in speech, spoken language ability, number cancelation, and combinations thereof.

10. A method of evaluating a cognitive state of a subject, the method comprising:
    providing a network of layers interconnected to form a convolutional neural network, the layers comprising a plurality of successive convolution layers and a plurality of fully connected layers;
    receiving reference data including a first data set associated with a plurality of physiological features and a second data set associated with a plurality of cognitive metrics, the first data set and the second data set being correlated by a respective time value;
    training the convolutional neural network using the reference data such that the plurality of successive convolution layers and the plurality of fully connected layers are adjusted in response to input from the first data set, the second data set, and the respective time values to construct a transformation function;
    receiving a data sample from the subject, the data sample including an input set of values associated with a respective plurality of physiological features of the subject;

selecting a predetermined time at which to evaluate the cognitive state of the subject, and determining a value for the selected predetermined time;

providing the input set of values and the value for the selected predetermined time to the transformation function, such that the transformation function is trained to predict a respective discrete value for each cognitive metric of the plurality of cognitive metrics from the input set of values and the value for the selected predetermined time; and determining the cognitive state of the subject at the selected predetermined time based on the predicted discrete values of the plurality of cognitive metrics.

11. The method of claim 10, wherein training the convolutional neural network comprises processing the first data set, the second data set, and the respective time values through a training mode configured to train a computer and construct the transformation function.

12. The method of claim 10, further comprising presenting the predicted discrete value for each of the cognitive metrics on a display.

13. The method of claim 10, comprising predicting the respective discrete value for each of the cognitive metrics by performing at least one calculation including:

adjusting the plurality of successive convolution layers in response to input from the input set of values to produce a plurality of convolution layer outputs; and adjusting the plurality of fully connected layers in response to the value for the selected predetermined time and the plurality of convolution layer outputs to produce the respective discrete value for each of the cognitive metrics.

14. The method of claim 13, further comprising receiving a second data sample from the subject at a later time and performing the at least one calculation to produce a second respective discrete value for each of the cognitive metrics.

15. The method of claim 14, further comprising training the convolutional neural network using a subject data set including:

the data sample, the second data sample, the respective discrete value for each of the cognitive metrics, and the second respective discrete value for each of the cognitive metrics to construct a customized transformation function.

16. The method of claim 10, comprising selecting the predetermined time to be up to ±36 months.

17. The method of claim 16, comprising selecting the predetermined time to be up to 36 months.

18. The method of claim 10, wherein the plurality of cognitive metrics include at least one of memory, practice, orientation, and language metrics.

19. The method of claim 18, wherein the plurality of cognitive metrics are selected from word recall, verbal commands, constructional praxis, delayed word recall, naming objects, ideation praxis, orientation, word recognition, test instructions recall, comprehension, word finding in speech, spoken language ability, number cancelation, and combinations thereof.

20. A cognitive evaluation system for predicting progression of a cognitive state of a subject, the system comprising:

a memory storing a reference data set including a first data set associated with a plurality of physiological features and a second data set associated with a plurality of cognitive metrics, the first data set and the second data set being correlated by a respective time value;

one or more processors coupled to the memory and configured to execute a cognitive state prediction component, the cognitive state prediction component configured to program the processor to:

receive a data sample from the subject, the data sample including a first set of values associated with a respective plurality of physiological features of the subject;

receive a time value corresponding to a selected predetermined time at which to evaluate the cognitive state of the subject;

provide the first set of values and the time value to a transformation function;

perform at least one calculation using the transformation function to predict a second set of values including a discrete value for each cognitive metric of a plurality of cognitive metrics from the first set of values and the time value; and display the discrete value for each cognitive metric on a display.

21. The system of claim 20, wherein the transformation function is constructed by:

receiving the reference data set; and training the cognitive state prediction component using the reference data set such that a convolutional neural network is adjusted in response to input from the reference data set to construct the transformation function.

22. The system of claim 20, wherein the cognitive state prediction component is further configured to program the processor to determine a probability of whether the subject is at risk for a mild cognitive impairment or Alzheimer's disease at the predetermined time based on the discrete value for each cognitive metric.

23. The system of claim 22, wherein the cognitive state prediction component is further configured to program the processor to display the probability on the display.

* * * * *